United States Patent
Janacek

Patent Number: 6,129,706
Date of Patent: Oct. 10, 2000

[54] CORRUGATED CATHETER BALLOON

[76] Inventor: Jaroslav Janacek, 56802 Svitavy-Lacmov 233, Czech Rep.

[21] Appl. No.: 09/209,146

[22] Filed: Dec. 10, 1998

[51] Int. Cl.[7] .................................................. A61M 29/00
[52] U.S. Cl. ........................................ 604/96; 604/103.08
[58] Field of Search .............................. 604/96, 101, 102, 604/103

[56] References Cited

U.S. PATENT DOCUMENTS

| | | |
|---|---|---|
| 4,941,877 | 7/1990 | Montano, Jr. . |
| 4,950,232 | 8/1990 | Ruzicka et al. . |
| 4,994,072 | 2/1991 | Bhate et al. . |
| 5,041,125 | 8/1991 | Montano, Jr. . |
| 5,087,246 | 2/1992 | Smith . |
| 5,192,296 | 3/1993 | Bhate et al. . |
| 5,250,070 | 10/1993 | Parodi . |
| 5,295,959 | 3/1994 | Gurbel et al. . |
| 5,306,246 | 4/1994 | Sahatjian et al. . |
| 5,308,356 | 5/1994 | Blackshear, Jr. et al. . |
| 5,318,587 | 6/1994 | Davey . |
| 5,342,301 | 8/1994 | Saab ........................................... 604/96 |
| 5,383,856 | 1/1995 | Bersin . |
| 5,409,458 | 4/1995 | Khairkhahan et al. . |
| 5,423,745 | 6/1995 | Todd et al. . |
| 5,458,572 | 10/1995 | Campbell et al. . |
| 5,478,319 | 12/1995 | Campbell et al. . |
| 5,484,411 | 1/1996 | Inderbitzen et al. . |
| 5,536,250 | 7/1996 | Klein et al. . |
| 5,545,132 | 8/1996 | Fagan et al. . |
| 5,549,625 | 8/1996 | Bircoll . |
| 5,554,119 | 9/1996 | Harrison et al. . |
| 5,599,306 | 2/1997 | Klein et al. . |
| 5,653,690 | 8/1997 | Booth et al. ............................... 604/96 |
| 5,693,014 | 12/1997 | Abele et al. . |
| 5,718,684 | 2/1998 | Gupta . |
| 5,720,726 | 2/1998 | Marcadis et al. ........................... 604/96 |
| 5,733,301 | 3/1998 | Forman . |
| 5,759,172 | 6/1998 | Weber et al. . |
| 5,792,415 | 8/1998 | Hijikema . |
| 5,807,331 | 9/1998 | den Heijer et al. . |

FOREIGN PATENT DOCUMENTS

| | | |
|---|---|---|
| 0485903 | 5/1992 | European Pat. Off. . |
| 0566684 | 10/1993 | European Pat. Off. . |
| WO8911306 | 11/1989 | WIPO . |
| WO9317748 | 9/1993 | WIPO . |
| WO9423787 | 10/1994 | WIPO . |
| WO9428963 | 12/1994 | WIPO . |
| WO9517223 | 6/1995 | WIPO . |
| WO9528985 | 11/1995 | WIPO . |
| WO9725093 | 7/1997 | WIPO . |

Primary Examiner—Mark O. Polutta
Assistant Examiner—Kelly M Cheney
Attorney, Agent, or Firm—Raymond Sun

[57] ABSTRACT

A catheter balloon is provided with a balloon body that includes at least one bump provided on the outer surface of the balloon body, with the bump being made in one piece with the balloon body. The bump can include a pattern of bumps provided on the outer surface of the balloon body, with the pattern of bumps assuming one of many configurations. A method is also provided for making a balloon for use with a catheter, including providing a tubing having an outer surface and at least one longitudinal bump provided integral with and in one piece with the tubing on the outer surface, and forming a balloon from the tubing.

5 Claims, 4 Drawing Sheets

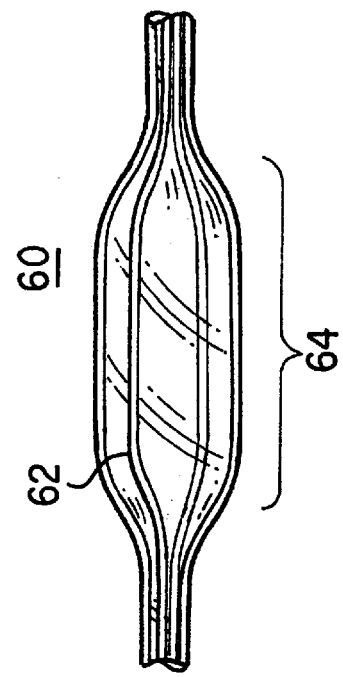
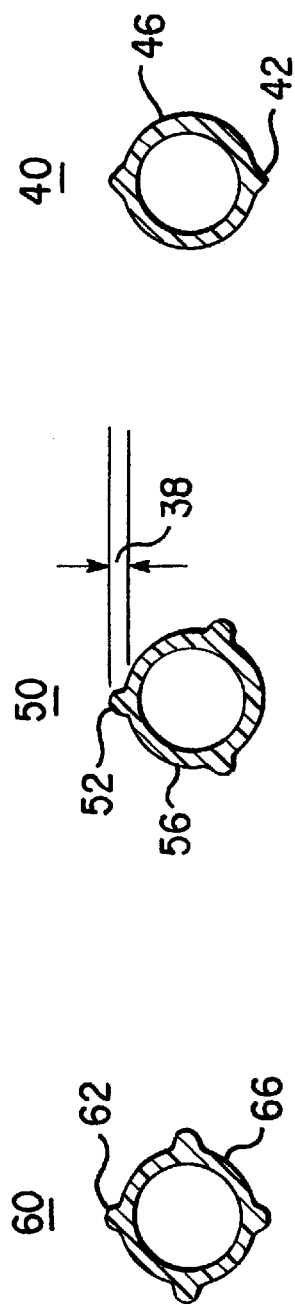
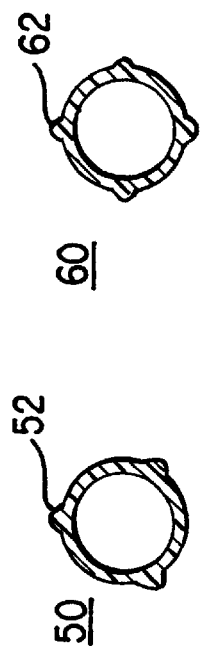

CORRUGATED CATHETER BALLOON

BACKGROUND OF THE INVENTION

1. Field of the Invention

The present invention relates to balloons that are used in connection with catheters, and in particular, corrugated balloons that can be adapted for use with dilatation catheters and catheters used to deliver intraluminal stents.

2. Description of the Prior Art

Catheter systems were initially provided for use during embolectomy and dilatation procedures to access intraluminal clots, thrombus, emboli or other deposits that have built up in the vessel. In a traditional embolectomy procedure, a catheter having a latex balloon is inserted into the lumen of the blood vessel so that the balloon extends beyond the clot, thrombus or deposit. The balloon is then inflated and pulled out of the vessel, dragging the clot, thrombus or deposit out of the vessel. In a traditional dilatation procedure, a catheter having a balloon is inserted into the lumen of the blood vessel so that the balloon is positioned in the region of the thrombus, emboli or deposit. The balloon is then inflated to break up the thrombus, emboli or deposit, by pushing it into the vessel wall. The catheter and its balloon are then removed from the vessel.

Recently, the development of endovascular stents and grafts have introduced an additional important function for balloon catheters: to carry, deliver and deploy intraluminal prosthesis such as stents and stent-grafts (also referred to hereinafter as "prosthesis"). In such an application, the prosthesis is compressed around the exterior of a deflated balloon. The catheter is then delivered intraluminally until the balloon is positioned at the desired stenting location in the vessel. Thereafter, the balloon is inflated to expand the prosthesis until the prosthesis engages the luminal wall of the vessel. The balloon is then deflated, and the catheter removed.

Conventional balloons are made from a polymeric material, with the most common examples being polyethylene (PE), nylon, silicon, or polyethylene terephthalate (PET). These conventional balloons typically have a generally oval configuration when expanded, and have a smooth and flat exterior surface.

Balloons made from PE, silicone or similar materials tend to be more compliant than balloons made from PET and nylon. As a result, PET and nylon balloons are favored for use in the delivery of prostheses. However, PET and nylon balloons have very thin walls that tend to be susceptible to mechanical damage (e.g., scratching, punching, tearing) and which may result in leakage of the balloon.

While conventional balloons have performed their embolectomy, dilatation and prosthesis-delivery functions relatively effectively, there are still unresolved problems associated with the use of conventional balloons for these procedures.

For example, the compliance of conventional balloons is relatively consistent throughout, which can be troublesome in certain circumstances. For example, balloons made from PE material exhibit greater compliance under higher pressures. This may cause over-dilation of the blood vessel, and in extreme cases, may cause the blood vessel to rupture. Some conventional balloons may also experience radial tearing when the balloon is expanded.

In addition, when used for dilatation, the generally oval expanded configuration of the conventional balloon with a smooth and flat exterior surface may sometimes be ineffective in dilating certain calcified or hard deposits, if these materials are particularly hard. This is because expansion of a relatively compliant balloon against very hard deposits may not cause the deposit to be dislodged or broken apart from the luminal wall.

When used for the delivery of prostheses, there is a significant concern that the prosthesis that is compressed over the non-inflated balloon will slip from or become mispositioned along the exterior surface of the balloon. This slippage or mispositioning is again a potential by-product of the smooth and flat exterior surface of a conventional balloon. Therefore, endovascular delivery systems that are provided to deliver prostheses often provide mechanisms (e.g., sleeves for covering the ends of the prosthesis) for holding the prosthesis securely over the non-inflated balloon. These mechanisms often complicate the design of the delivery systems and increase the costs thereof.

In addition, effective deployment of the entire length of the prosthesis requires the balloon to have generally the same outer diameter throughout when expanded. In this regard, the normal oval configuration of an expanded balloon makes it difficult to achieve this objective. To address this problem, a number of efforts have been made, such as to provide longer balloons, and to provide balloons that are constrained at both ends to cause the balloon to assume a "square" configuration when expanded, among others. However, longer balloons complicate the design of the delivery system and catheter. In addition, balloons having constrained ends are susceptible to experiencing a "dog-bone" effect when expanded, where both ends of the balloon are wider than the central portion of the balloon, resembling the shape of a dog-bone. The "dog-bone" effect can be potentially dangerous to the patient because the ends of the expanded prosthesis tend to have a larger diameter than the central portions, and therefore may cut or otherwise rupture the wall of the vessel into which the prosthesis is being deployed.

Thus, there still exists a need for balloons that can be used effectively for both dilatation and the delivery of prosthesis, which help to reduce the complexity of catheter devices used for these procedures, which have a simple structure, and which are easy and inexpensive to manufacture.

SUMMARY OF THE DISCLOSURE

In order to accomplish the objects of the present invention, there is provided a balloon for use with a catheter, the balloon having a balloon body that includes at least one bump provided on the outer surface of the balloon body and being made in one piece with the balloon body.

In one embodiment, the at least one bump includes a pattern of bumps provided on the outer surface of the balloon body. The pattern of bumps can assume one of many configurations. For example, the pattern can be an uninterrupted helical pattern extending across the balloon from the first end to the second end. As another example, the pattern can be a helical pattern provided adjacent opposite first and second ends of the balloon, with the central portion of the balloon being devoid of a helical pattern. As another example, the pattern can be a helical pattern provided at the central portion of the balloon, with opposite first and second ends of the balloon being devoid of a helical pattern.

The present invention also provides a method of making a balloon for use with a catheter, including providing a tubing having an outer surface and at least one longitudinal bump provided integral with and in one piece with the tubing on the outer surface, and forming a balloon from the tubing.

In one embodiment, the method can include forming a configuration for the at least one longitudinal bump on the outer surface of the balloon. The configuration can be formed by twisting opposing ends of the balloon. It is also possible to subject selected portions of the outer surface of the balloon to heat during the twisting.

BRIEF DESCRIPTION OF THE DRAWINGS

FIGS. 2A, 2B and 2C are cross-sectional views of extruded balloon tubings having a different number of radial bumps;

FIG. 3A is a side perspective view of an expanded extruded balloon tubing having three radial bumps;

FIG. 3B is a cross-sectional view of the tubing of FIG. 3A;

FIG. 4A is a side perspective view of an extruded balloon tubing having four radial bumps;

FIG. 4B is a cross-sectional view of the tubing of FIG. 4A;

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

The present invention provides corrugated balloons having strips or bumps (also referred to herein as "corrugations") extending radially from the exterior surface of the balloon. The corrugations can be provided in any configuration, and can be configured differently at different parts of the balloon. The present invention also provides simple and cost-effective methods of manufacturing the corrugated balloons.

Figure 1:
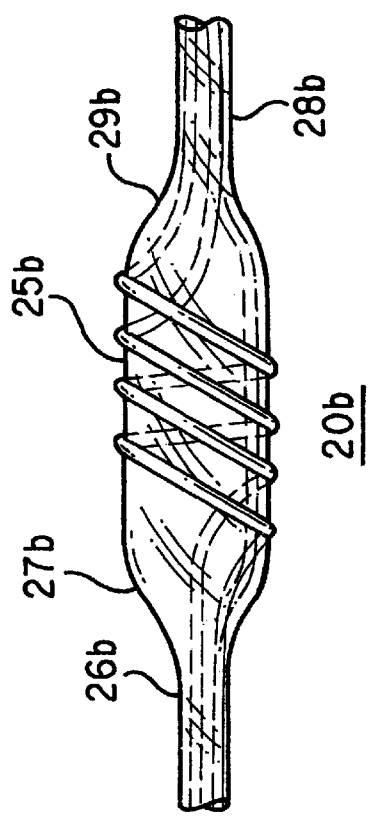
FIG. 1 is a perspective view of a balloon according to one embodiment of the present invention.

The basic principles of the present invention are illustrated by the balloon 20 in FIG. 1. The balloon 20 has a pair of intersecting helical corrugations or bumps 22 and 24, each of which extends from a first end 26 of the balloon 20 to a second end 28.

Figure 5:
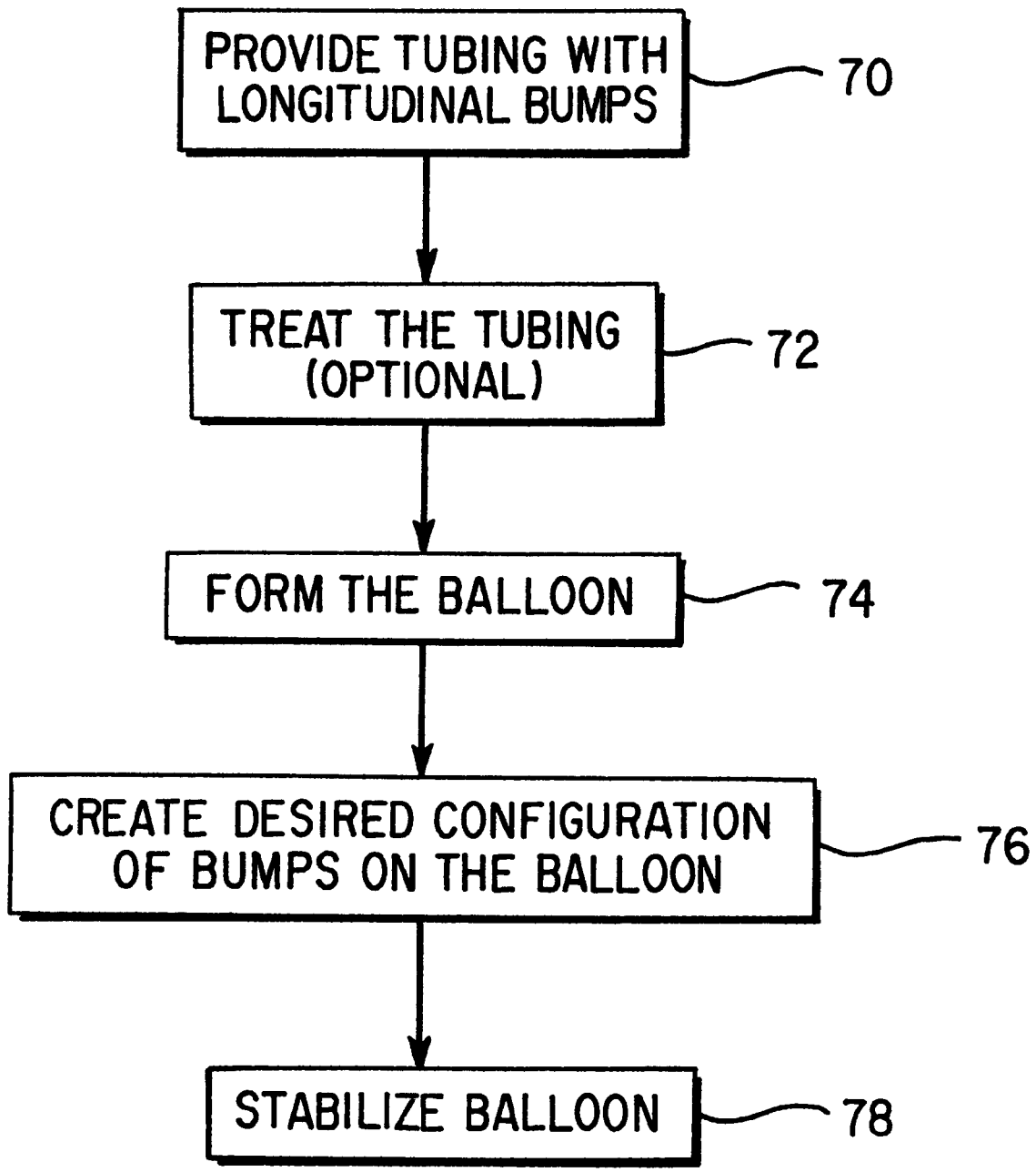
FIG. 5 is a flow-chart illustrating a method of forming a corrugated balloon according to the present invention.

FIGS. 2–4 illustrate how the balloon 20, and similar balloons, can be made. FIG. 5 is a flowchart illustrating the steps of the method of the present invention. In the first step 70, a conventional balloon tubing is extruded to provide an extruded tubing. The tubing can be a material used for forming conventional balloons, and is preferably less compliant and has a higher burst pressure. Examples of this material include polyethylene (PE), nylon, PET and silicone. In a preferred example, the material can be a high-density PE. Such conventional tubings are typically extruded together with a plurality of bumps or corrugations that are provided in the same material as the tubing, so that the resulting tubing and bumps are provided as one piece. As an alternative, the bumps can be provided in a material (e.g., PE, nylon, PET or silicone) that is different from the material of the tubing, and then co-extruded with the tubing, again to provide the resulting tubing and bumps as one piece.

For example, FIGS. 2A, 2B and 2C illustrate tubings 40, 50 and 60 having two, three and four longitudinal bumps 42, 52 and 62, respectively, that extend radially from the exterior surface 46, 56, 66 of the tubing. Any of these tubings 40, 50, 60 can be used to form the balloon 20 of FIG. 1, since balloon 20 can be formed by a tubing having any number of bumps by varying the number of twists (as explained below) that are applied to the tubing. Returning to FIGS. 2A, 2B and 2C, any number of bumps (i.e., two or more) can be provided for each tubing. In one embodiment, the bumps 42, 52, 62 can be spaced-apart from each other in an equi-distant manner about the circumference of the respective tubing 40, 50 or 60. These tubings 40, 50, 60 have a consistent configuration throughout their lengths after the extrusion step. As can be seen, the bumps 42, 52, 62 provide an increased wall thickness (see 38 in FIG. 2B) in the wall of the balloon. The thicknesses of the bumps 42, 52, 62 can also be varied, and designed according to the particular application or need. In addition, the bumps 42, 52, 62 can have different shapes. For example, bumps 42 in FIG. 2A can be generally triangular, while the bumps 52 and 62 in FIGS. 2B and 2C, respectively, can be generally curved or rounded. Moreover, the tubing can be co-extruded from different densities. For example, the body of the tubing can be a low-density PE material, while the bumps can be a high-density PE. The high-density PE is less compliant so it has a higher burst pressure.

In the second step 72, the extruded tubing may be treated. The treatment will vary depending upon the nature of the material used. For example, a PE tubing is treated by electrobeams (i.e., irradiation) to change the molecular structure of the tubing material to allow it to be expanded. Irradiated PE tubing has similar properties as shrink tubing. On the other hand, PET, nylon and silicone do not need to be treated.

In the third step 74, the balloon is then formed from the tubing. The balloon can be molded by hand, or formed in a conventional balloon-forming machine using temperature, axial stretch and controlled force of the stretch with pressure (as known in the art) to expand the tubing into the desired shape of the balloon. FIGS. 3A, 3B, 4A and 4B illustrate what the tubing looks like after the balloon has been formed. In particular, the tubings 50 and 60 are shown in FIGS. 3 and 4, respectively. In FIGS. 3A and 3B, the tubing 50 is shown with the formed balloon 54 having three longitudinal bumps 52 that extend radially from the exterior surface 56 of the balloon 54. Similarly, in FIGS. 4A and 4B, the tubing 60 is shown with the formed balloon 64 having four longitudinal bumps 62 that extend radially from the exterior surface 66 of the balloon 64.

In the fourth step 76, the desired configuration of the corrugations or bumps is created on the formed balloon of the extruded tubing. Referring to FIG. 1, this can be accomplished in general by gripping the ends 26 and 28 of the balloon 20, and then twisting the balloon 20 in opposite directions. The twisting is performed under appropriate temperatures (e.g., about 300 degrees Fahrenheit), pressures (e.g., 40 PSI), and axial stretch (e.g., 200% stretch). The gripping and twisting can be done by a pair of human hands, or by a customized machine or robot that is built for this application. The gripping and twisting will cause the longitudinal bumps 22 and 24 to form a helical pattern, so that adjacent longitudinal bumps 22 and 24 will form intersecting helixes as shown in FIG. 1. In FIG. 1, the helical corrugations or bumps 22, 24 extend in a uniform and consistent manner from one end 26 to the other end 28 of the balloon 20. If the twisting is done manually (i.e., by hand), the maker can view the emerging helical pattern as he or she is twisting the balloon 20, so that the maker can then decide on the exact helical pattern that is desired. For example, adding a few additional twists will result in a smaller pitch between adjacent helixes in the resulting helical pattern.

Thereafter, in the fifth step 78, the corrugated balloon is stabilized (e.g., removing the balloon from a heated zone and then allowing it to cool) using appropriate temperatures (e.g., 120–180 degrees Fahrenheit) and pressures (e.g., 40–50 psi) to fix the configuration of the balloon and its corrugation pattern.

Figure 6:
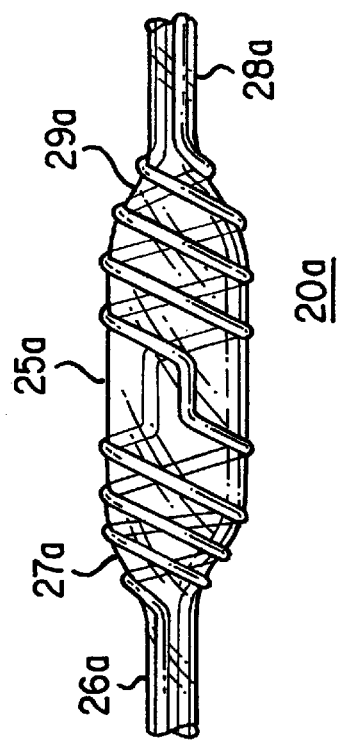
FIG. 6 is a perspective view of a balloon according to another embodiment of the present invention.

Different patterns of corrugations can be formed on the balloon 20. For example, FIG. 6 illustrates a balloon 20a having generally helical corrugations adjacent the ends or necks 26a, 28a of the balloon 20a, with the corrugations at the center portion of the balloon 20a having a simple longitudinal pattern. This pattern of corrugations is especially useful for use in the delivery of a prosthesis, since the helical corrugations at both ends 26a, 28a of the balloon 20a provide grooves and an uneven surface that are effective in preventing slippage of the prosthesis. In addition, this pattern of corrugations can minimize the "dog-bone" effect because the ends 26a, 28a are less compliant than the middle section of the balloon 26a (which has fewer helical corrugations).

Figure 7:
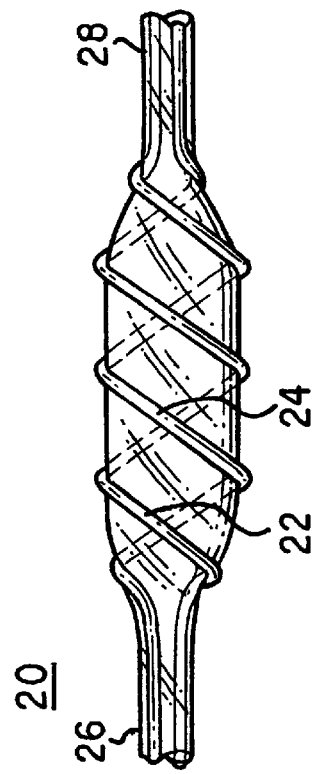
FIG. 7 is a perspective view of a balloon according to yet another embodiment of the present invention.

As another example, FIG. 7 illustrates a balloon 20b having generally helical corrugations at the center portion 25b thereof, with the corrugations at the tapered portions 27b, 29b adjacent the ends 26b, 28b of the balloon 20b having a simple longitudinal pattern. This pattern of corrugations renders the center portion 25b more compliant than the tapered portions 27b, 29b, and is especially useful for use in stent sizing.

The different corrugation patterns illustrated in FIGS. 6 and 7 can be easily formed by covering the portions of the balloon where the twisting (i.e., helix) is to be absent, and then applying a heat source only to the exposed portions where twisting is to occur. For example, the heat can be provided by hot air blown from a heat torch. The twisting action can then be applied simultaneously with the application of the heat. In one embodiment, the covering can be accomplished by using the fingers of a hand or a sheet of material.

Figure 9:
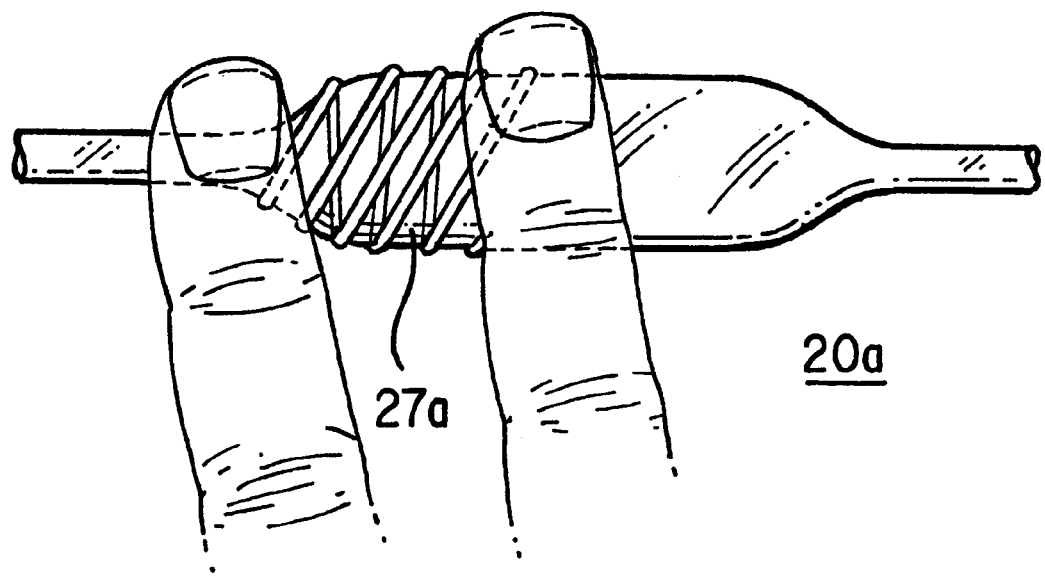
FIG. 9 illustrates another method of forming a helical pattern of corrugations for the balloon of FIG. 6.

For example, referring to FIG. 9, two fingers can be used to cover the end 26a and the center portion 25a of the balloon 20a to form corrugations or twists at the tapered portion 27a, but not at the center portion 25a, with the heat being applied to the tapered portion 27a only. Then, the two fingers can be used to cover the end 28a and the center portion 25a of the balloon 20a to form corrugations or twists at the tapered portion 29a, but not at the center portion 25a, with the heat being applied to the tapered portion 29a only.

Figure 8:
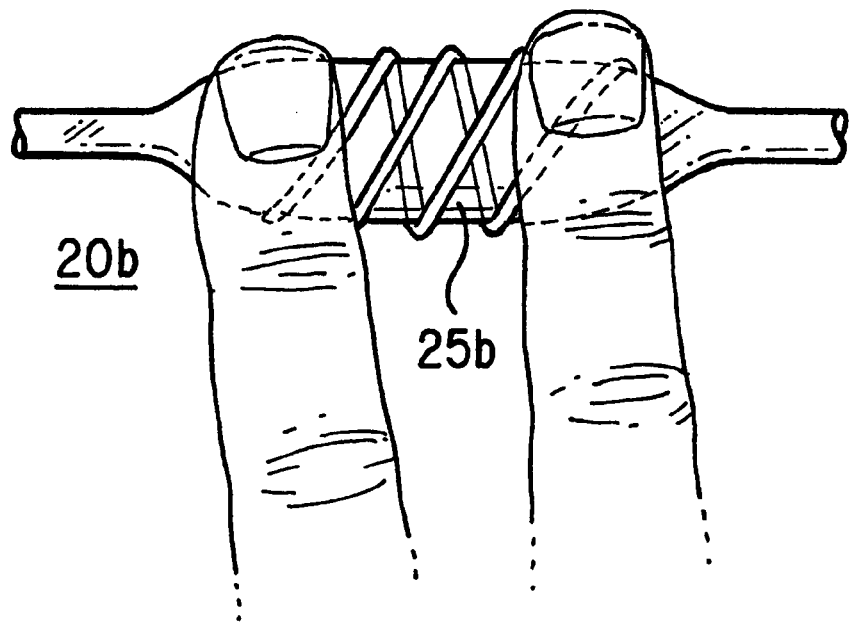
FIG. 8 illustrates one method of forming a helical pattern of corrugations for the balloon of FIG. 7.

As another example, referring to FIG. 8, two fingers can be used to cover the tapered portions 27b and 29b adjacent the two ends 26b and 28b, respectively, of the balloon 20b, to form corrugations or twists at the center portion 25b, but not at the tapered portions 27b, 29b. The heat would be applied to the center portion 25b only.

In FIG. 1, the balloon 20 would not be covered, and heat would be applied to the entire balloon 20 during twisting.

Thus, the corrugated balloons of the present invention are formed without (1) the use of glue, (2) the cutting or engraving of the surface of the balloon wall, and (2) the application of separate strips of material after the balloon has been formed. These features enable the corrugated balloons of the present invention to be provided in a cost-effective and reliable manner that renders the balloons safe and effective in use.

The corrugated balloons of the present invention are also effective in addressing the problems described above. In particular, the corrugated balloons of the present invention have different compliances along the bumps or corrugations, thereby being well-suited for use with stents or prostheses having different resistance characteristics. This would allow the physician to more easily and accurately position and set the prostheses inside the lumen of a vessel. In addition, the varying wall thickness of the corrugated balloons of the present invention provide different wall thicknesses to minimize radial tearing of the balloon. Moreover, the corrugations provide grooves and an uneven surface that are effective in preventing slippage of a prosthesis when used to deliver such prosthesis. Further, the corrugations help the balloon attain generally the same outer diameter throughout during radial expansion of the balloon and axial expansion of the prosthesis. When used for dilatation, the varying thicknesses of the bumps or corrugations are effective in dislodging or breaking up the calcified or hard deposits.

The present invention provides yet another benefit in that different outer diameters of the expanded balloon can be controlled and made by changing the density and directions of the corrugation patterns. In other words, the number of corrugations and the density of the twists can be varied to obtain the desired outer diameters, and the desired compliance at the balloon wall.

The corrugated balloons of the present invention can be used in connection with any conventional catheter, including over-the-wire, rapid-exchange, or fixed-wire catheters.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A balloon for use with a catheter, comprising a balloon body made from a material and having an outer surface, a first end, a second end and a central portion, the balloon further including a helical corrugated pattern provided on the outer surface of the balloon body and being made in one piece with the balloon body, wherein the helical corrugated pattern is provided adjacent the first and second ends of the balloon, with the central portion of the balloon being devoid of a helical corrugated pattern.

2. The balloon of claim 1, wherein the material is selected from the group consisting of PET, PE, silicone and nylon.

3. The balloon of claim 1, wherein the helical corrugated pattern is made from a material that is different from the material for the balloon body, the helical corrugated pattern being coextruded with the balloon body.

4. The balloon of claim 1, wherein the balloon has a first end, a second end and a central portion, and wherein the first and second ends have a different compliance than the central portion.

5. The balloon of claim 1, wherein the balloon is less compliant at the region of the helical corrugated pattern than at other portions of the balloon.

* * * * *